(12) United States Patent
Fortin

(10) Patent No.: US 6,375,355 B1
(45) Date of Patent: Apr. 23, 2002

(54) MOVEABLE TABLE

(76) Inventor: Joseph Fortin, 7230 Engle Rd., Suite 210, Fort Wayne, IN (US) 46804

(*) Notice: Subject to any disclaimer, the term of this patent is extended or adjusted under 35 U.S.C. 154(b) by 0 days.

(21) Appl. No.: 09/521,820

(22) Filed: Mar. 9, 2000

Related U.S. Application Data

(60) Provisional application No. 60/123,614, filed on Mar. 10, 1999.

(51) Int. Cl.[7] .................................................. A61B 6/04
(52) U.S. Cl. ........................................ 378/209; 378/208
(58) Field of Search ............................... 378/209, 208, 378/195, 196; 5/600, 601

(56) References Cited

U.S. PATENT DOCUMENTS

| | | |
|---|---|---|
| 3,053,568 A | 9/1962 | Miller |
| 3,504,179 A | 3/1970 | Hainault |
| 3,670,163 A | 6/1972 | Lajus |
| 3,818,516 A * | 6/1974 | Hopper et al. ............. 378/209 |
| 3,967,126 A | 6/1976 | Otto, Jr. |
| 4,156,815 A | 5/1979 | Hogan |
| 4,896,917 A | 1/1990 | Enevoldson |
| 5,013,018 A | 5/1991 | Sicek et al. |
| 5,490,297 A | 2/1996 | Bradcovich et al. |
| 5,499,415 A * | 3/1996 | McKenna ...................... 5/601 |
| 5,517,991 A * | 5/1996 | Hermann et al. ........... 378/209 |
| 5,572,569 A | 11/1996 | Benoit et al. |
| 5,661,859 A | 9/1997 | Schaefer |

* cited by examiner

Primary Examiner—David P. Porta
(74) Attorney, Agent, or Firm—Randall J. Knuth

(57) ABSTRACT

An X-ray table supported above a base for use with a C-arm X-ray machine, including an X-ray permeable table surface. The table also includes at least two support members for supporting the table above the base with at least two support members and the base forming a substantially unobstructed middle area, a first one of at least two support members pivotally connected to the base, a second one of at least two support members being fixedly connected to the base, and an actuator for moving the table with two degrees of freedom. The actuator is pivotally connected to the table and fixedly connected to at least two support members.

16 Claims, 3 Drawing Sheets

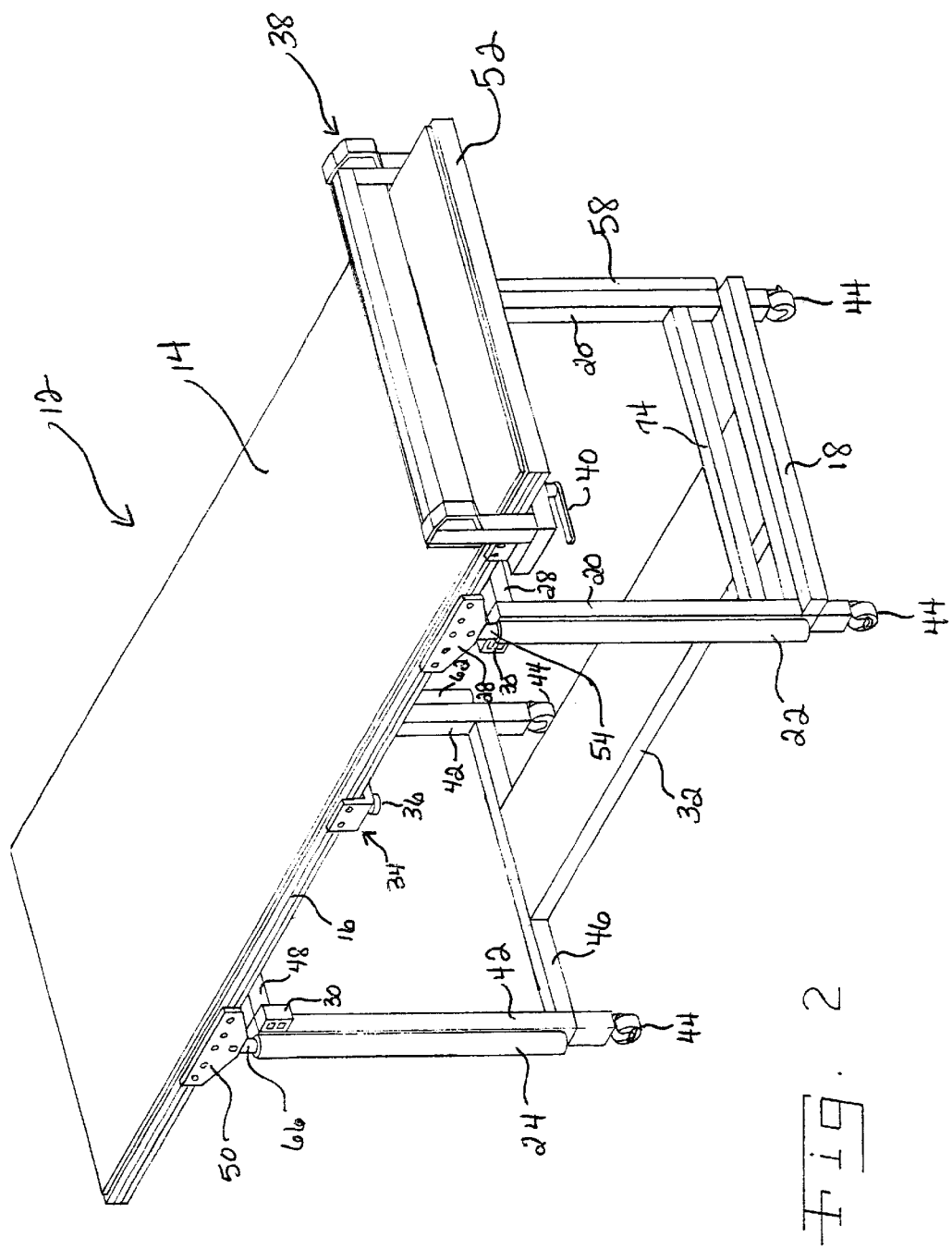

MOVEABLE TABLE

This appln claims benefit of provisional application No. 60/123,614 filed Mar. 10, 1999.

BACKGROUND OF THE INVENTION

1. Field of the Invention

The present invention relates to moveable tables and, more particularly, to moveable tables which are adapted for use with a C-arm X-ray machine.

2. Description of the Related Art.

X-ray tables for supporting patients during X-ray imaging which can be height adjusted and tilted to achieve trendelenburg and reverse trendelenburg positions are useful in the art of X-ray imaging. Conventional fluoroscope X-ray tables contain an X-ray machine underneath the table top and therefore do not allow for the convenient use of a C-arm X-ray machine.

The desire to create an X-ray table which can be used with a C-arm X-ray machine has led to the creation of X-ray tables which are laterally extended from a support column so that one side of the laterally extended table has open portions above and below the table to accommodate a C-arm X-ray machine. X-ray tables of this type require a large base and support column to support the laterally extending table and to avoid tipping of the table when a patient occupies the table top.

Additionally, tables have been designed so that the table top will laterally move from a position above the table base and support structure to a position substantially laterally removed from above the support structure. In this way, a C-arm X-ray machine may be used when the table top has been moved to a position which is substantially removed from its support structure. Tables of this kind require a large room to accommodate the lateral movement of the X-ray table. Additionally, these X-ray tables must also be of considerable size and weight to support a patient lying on the table in its extended position.

The ability to accommodate a C-arm X-ray machine as described in the above-mentioned configurations is desirable, however, the increased size and weight of the above described X-ray tables is problematic. These large, heavy tables are expensive and require rooms designed to accommodate the significant weight of these tables. The significant weight of the above-mentioned tables also presents mobility problems for these tables. Additionally, tables which employ a laterally moving table top require an X-ray room of increased size to accommodate the table in its extended position. Further, table configurations which include a laterally extending X-ray table accommodate C-arm X-ray machines on only one side of the table. In this way, these tables are of limited versatility. Currently, the purchaser of an X-ray table cannot utilize a C-arm X-ray machine without providing a room which will accommodate the significant weight of the aforementioned tables as well as the increased length of the table if a laterally moving table top is employed. Additionally, a current purchaser of an X-ray table which is designed for use with a C-arm X-ray machine must deal with the mobility problems associated with the current large and heavy tables.

SUMMARY OF THE INVENTION

The present invention is directed to improve upon the aforementioned X-ray tables wherein it is desired to provide an X-ray table which will accommodate a C-arm X-ray machine, is smaller and lighter than X-ray tables of the prior art and is versatile in its use.

The present invention provides an X-ray table which accommodates a C-arm X-ray machine on either side of the X-ray table, is light and is small in size.

The invention, in one form thereof, comprises an X-ray table for use with a C-arm X-ray machine which includes an X-ray permeable table and at least two support members for supporting the table above a base. In this form, the support members, the X-ray table, and the base form a substantially unobstructed area which will accommodate a C-arm X-ray machine on either side of the table.

The invention, in another form thereof, comprises an X-ray permeable table, a base, at least two vertical support members and at least two actuators. The actuators can be, for example, hydraulic cylinders. The at least two actuators are affixed to the at least two vertical support members and are pivotally connected to the X-ray table. One vertical support member is pivotally connected to the base. Another vertical support member is fixedly connected to the base. The at least two actuators provide for height adjustment of the table. The at least two actuators also provide a means for moving the table into the trendelenburg and reverse trendelenburg positions.

The invention, in another form thereof, comprises an X-ray permeable table, a base, at least two vertical support members, and an actuator. The actuator can be, for example, a hydraulic cylinder. The actuator is affixed to the vertical support member and is pivotally connected to the X-ray table. The support member to which the actuator is affixed is pivotally connected to the base. A vertical support member not attached to the actuator is pivotally connected to the X-ray table and is fixedly to the base. The actuator provides a means for moving the table into the trendelenburg and reverse trendelenburg positions.

The invention, in another form thereof, includes an X-ray table supported by aluminum frame members which form a base and vertical supports.

The invention, in another form thereof, comprises frame members which form a base and vertical supports, actuators which are affixed to the vertical supports, and a removable X-ray table which is attached to the actuators and may be removed and replaced with an X-ray permeable chair.

The invention, in another form thereof, includes an X-ray permeable table top which is supported by at least two support members which support the X-ray table above a base. In this form, the X-ray permeable table top is surrounded by extruded rails, which are, for example, made of aluminum. The extruded rails include an opposing pair of extruded side rails and an opposing pair of extruded end rails. In this form, an adjustable foot rail is movably fixed to the opposing pair of aluminum extruded side rails.

The invention, in another form thereof, includes a polypropylene, X-ray permeable table which is mounted on frame members which form a base and vertical support members. Actuators are affixed to the vertical support members and to the polypropylene table.

The invention, in another form thereof, includes frame members, which can, for example, be made from aluminum, which form a base and vertical support members. Actuators are affixed to the vertical support members and are pivotally connected to an X-ray table. Actuator controllers are operatively connected to the actuators. In this form, electric motors are operatively connected to both the actuator controllers and the actuators and provide a means for actuating the hydraulic cylinders so that the table may be horizontally moved as well as being placed in the trendelenburg and reverse trendelenburg positions.

The invention, in another form thereof, includes frame members which form a base and vertical support members. The vertical support members support an X-ray table and have lockable wheels affixed to the ends opposite the X-ray table.

The invention, in another form thereof, includes an X-ray table which is surrounded by extruded rails which are, for example, made from aluminum. Frame members form a base and vertical supports. Actuators which are, for example, hydraulic cylinders, are affixed to the vertical supports and to the extruded rails of the X-ray table. Actuator controllers are provided and control the actuators so that the table may be height adjusted as well as being placed both in the trendelenburg and reverse trendelenburg positions. In this form, the aluminum extruded rails are removably fixed to the X-ray table and may be replaced with extruded rails which are made from material which is clear to X-ray radiation or does not interfere with X-ray usage.

The invention, in another form thereof, includes an X-ray table which is surrounded by extruded rails which are, for example, made of aluminum. Frame members form a base and vertical supports. Actuators are affixed to the vertical supports and to the extruded rails of the X-ray table so that the X-ray table may be height adjusted, and placed in the trendelenburg or reverse trendelenburg position. At least one accessory support, which provides for accessary attachment to the table, is movably attached to an extruded rail. The accessory support includes a screw adjustment knob for fixing the position of the accessory support.

An advantage of the present invention is the ability to provide an X-ray table which is versatile in use and can accommodate a C-arm X-ray machine on any side.

Another advantage of the present invention is the ability to interchangeably use an X-ray table or X-ray chair with the same base structure and hydraulic movement system, which accommodates a C-arm X-ray machine.

Another advantage of the present invention is the ability to provide a small and light weight X-ray table which will accommodate a C-arm X-ray machine.

Another advantage of the present invention is to provide an X-ray table which will accommodate a C-arm X-ray machine and does not require a room designed to accommodate heavy machinery.

Another advantage of the present invention is the ability to provide an X-ray table which will accommodate a C-arm X-ray machine and does not require a room which is large enough to accommodate a laterally moveable X-ray table top.

A further advantage of the present invention is the ability to provide an X-ray table which will accommodate a C-arm X-ray machine and which is small and light weight and can therefore be easily moved.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 2 is a perspective view of an X-ray table of the present invention;

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
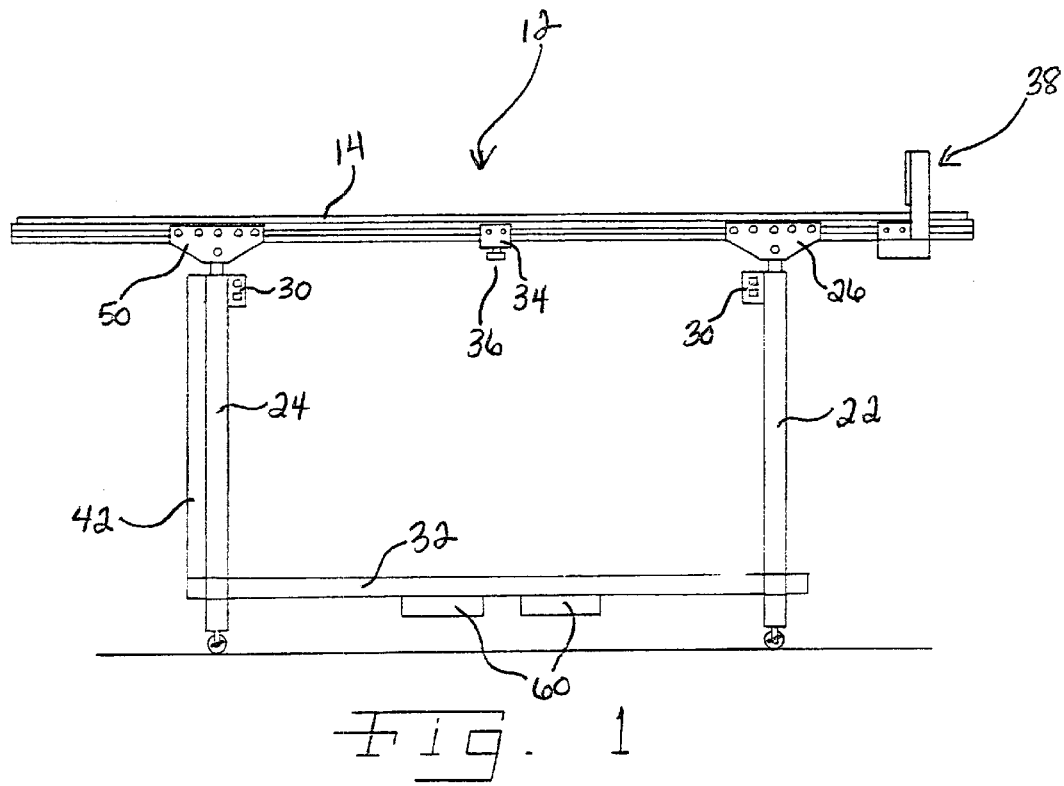
FIG. 1 is a front elevational view of an X-ray table of the present invention.

Referring now to the drawings and particularly to FIG. 1, there is shown a moveable table 12. X-ray permeable table top 14 is supported above base member 32 by first and second hydraulic cylinders 22 and 58 and third and fourth hydraulic cylinders 62 and 24, forming a substantially unobstructed area which will accommodate a C-arm X-ray machine.

FIG. 1 illustrates moveable table 12 including electric motors 60, which provide for actuation of first and second hydraulic cylinders 22 and 58 and/or third and fourth hydraulic cylinders 62 and 24.

Figure 3:
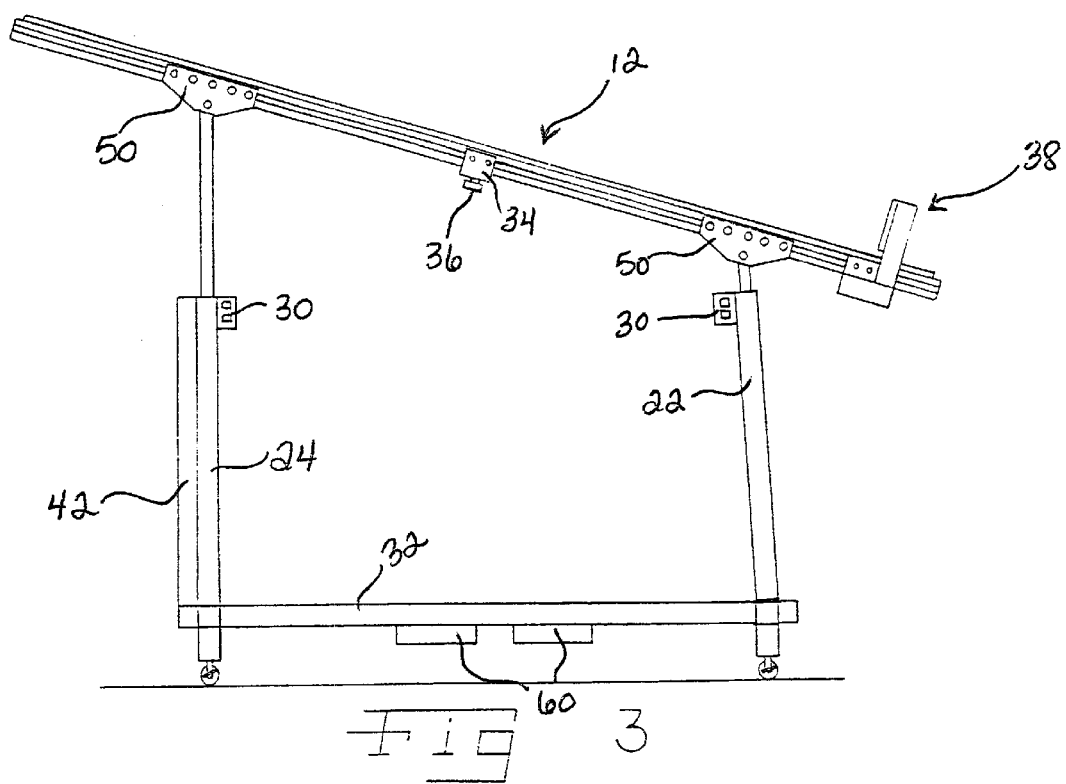
FIG. 3 is a front elevational view showing actuation of a pair of hydraulic cylinders so that the table is in the reverse trendelenburg position.

FIG. 3 illustrates moveable table 12 in the reverse trendelenburg position. Third and fourth hydraulic cylinders 62 and 24 are actuated causing vertical movement of one end of X-ray permeable table top 14. As illustrated, first and second hydraulic cylinders 22 and 58 pivot away from vertical to accommodate this position of moveable table 12.

Figure 4:
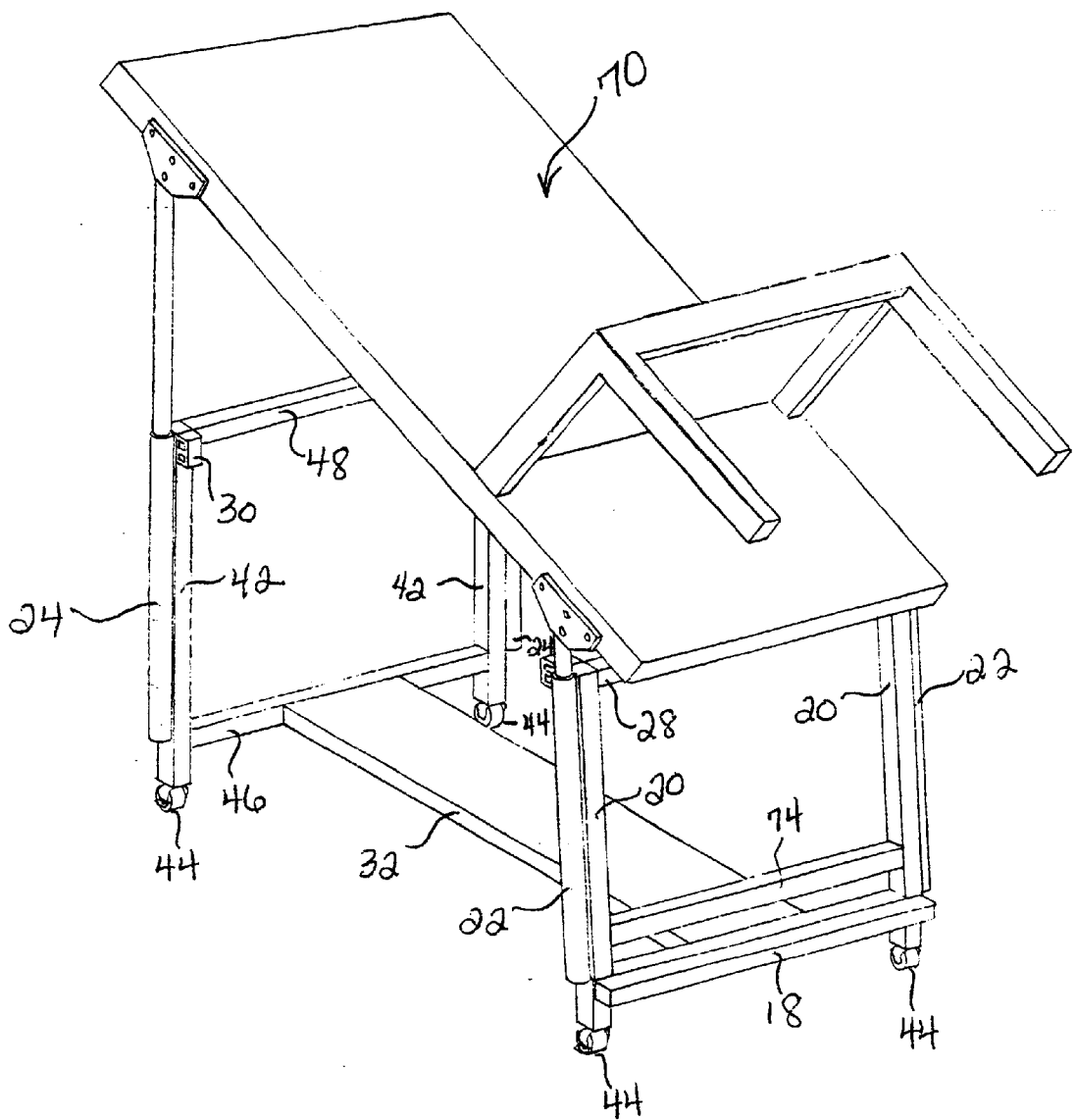
FIG. 4 is a perspective view of an alternate embodiment of the present invention incorporating an X-ray permeable chair attached to the hydraulic cylinders.

FIG. 4 illustrates an alternative embodiment of the present invention wherein X-ray permeable table top 14 (FIG. 2) has been removed and replaced with X-ray permeable chair 70.

Referring now to FIG. 2, there is shown a moveable table 12. Moveable table 12 has an X-ray permeable table top 14 which is surrounded by aluminum extruded rails 16, 52 and rails opposite rails 16, 52 (not shown). First lower end brace 18 is fixedly connected to base member 32. First vertical frame members 20 are pivotally connected to first lower end brace 18. Lateral brace 74 is affixed to first vertical frame members 20 and extends there between. Second lower end brace 46 is fixedly connected at both ends to second vertical frame members 42. First upper end brace 28 is fixedly attached at either end to first vertical frame members 20. Second upper end brace 48 is fixedly connected at both ends to second vertical frame members 42.

Lockable wheels 44 are affixed to opposite ends of first lower end brace 18 and second lower end brace 46.

First hydraulic piston 54 is pivotally attached to first side plate 26. Second hydraulic piston (not shown) extends from second hydraulic cylinder 58 and is pivotally attached to second side plate (not shown). First and second hydraulic cylinders 22 and 58 are fixedly connected to first vertical frame members 20. Third and fourth hydraulic cylinders 62 and 24 are fixedly connected to second vertical frame members 42. Fourth hydraulic piston 66 is pivotally attached to fourth side plate 5O. Third hydraulic piston (not shown) extends from third hydraulic cylinder 62 and is pivotally attached to third side plate (not shown). Controllers 30 are fixedly attached to a first vertical frame member 20 and a second vertical frame member 42.

Base member 32 is fixedly attached at either end to first and second lower end braces 18 and 46. Accessory support 34 is movably attached to aluminum extruded rail 16. Accessory support 34 includes screw adjustment knob 36 for fixing the position of accessory support 34.

Adjustable foot rail 38 is movably fixed to aluminum extruded rail 16 and to an opposing aluminum extruded rail (not shown). Adjustable foot rail 38 includes a first locking lever 40 and a second locking lever (not shown). Adjustable foot rail 38 may be locked in various positions between first and second side plates 26, (not shown) and aluminum extruded rail 52.

Prior to an X-ray procedure, the adjustable foot rail 38 (FIG. 2) is moved into an appropriate position to accommodate the particular patient on which the X-ray procedure is to be performed. The patient will then take his/her position on the X-ray table. Any necessary accessories may then be attached to accessory support 34 which will be fixed in place along aluminum extruded rail 16 by means of screw adjustment knob 36. During an X-ray procedure, an X-ray technician or operator may utilize controllers 30 to actuate first and second hydraulic cylinders 22, and 58 and/or third and fourth hydraulic cylinders 62 and 24 to achieve a desired patient position including, a horizontally raised position, the trendelenburg position or the reverse trendelenburg position. The large open space created between the X-ray permeable table top 14 or X-ray permeable chair 70 (FIG. 4), first vertical frame members 20, second vertical frame members 42 and base member 32 allows this table to easily accommodate a C-arm X-ray machine.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An X-ray table supported above a base for use with a C-arm X-ray machine, comprising:

an X-ray permeable table surface;

at least two support members for supporting said table above the base, said at least two support members and the base forming a substantially unobstructed middle area, a first one of said at least two support members pivotally connected to the base, a second one of said at least two support members being fixedly connected to the base; and an actuator for moving said table with two degrees of freedom, said an actuator pivotally connected to said table and fixedly connected to said at least two support members.

2. An X-ray table supported above a base for use with a C-arm X-ray machine, comprising:

an X-ray permeable table surface;

at least two support members for supporting said table above the base, said at least two support members and the base forming a substantially unobstructed middle area, a first one of said at least two support members pivotally connected to the base, a second one of said at least two support members being fixedly connected to the base; and at least two actuators for moving said table with at least two degrees of freedom, said at least two actuators pivotally connected to said table and fixedly connected to said at least two support members.

3. An X-ray chair supported above a base for use with a C-arm X-ray machine, comprising:

an X-ray permeable chair;

at least two support members for supporting said chair above the base, said at least two support members and the base forming a substantially unobstructed middle area, a first one of said at least two support members pivotally connected to the base, a second one of said at least two support members being fixedly connected to the base; and an actuator for moving said chair with two degrees of freedom, said an actuator pivotally connected to said chair and fixedly connected said at least two support members.

4. An X-ray chair supported above a base for use with a C-arm X-ray machine, comprising:

an X-ray permeable chair;

at least two support members for supporting said chair above the base, said at least two support members and the base forming a substantially unobstructed middle area, a first one of said at least two support members pivotally connected to the base, a second one of said at least two support members being fixedly connected to the base; and at least two actuators for moving said chair with at least two degrees of freedom, said at least two actuators pivotally connected to said chair and fixedly connected said at least two support members.

5. The X-ray table in claim 1 wherein said actuator is a hydraulic cylinder.

6. The X-ray table in claim 1 wherein said actuator moves said X-ray table into a trendelenburg position.

7. The X-ray table in claim 1 wherein at least one rail is attached to said X-ray table and said at least one rail is transparent to X-ray radiation.

8. The X-ray table in claim 2 wherein said at least two actuators change the height of said X-ray table.

9. The X-ray table in claim 2 wherein said at least two actuators move said X-ray table into a reverse trendelenburg position.

10. The X-ray table in claim 2 wherein at least one rail is attached to said X-ray table and said at least one rail is transparent to X-ray radiation.

11. The X-ray chair in claim 3 wherein said actuator changes the height of said X-ray chair.

12. The X-ray chair in claim 3 wherein said actuator moves said X-ray chair into a reverse trendelenburg position.

13. The X-ray chair in claim 3 wherein at least one rail is attached to said X-ray chair and said at least one rail is transparent to X-ray radiation.

14. The X-ray chair in claim 4 wherein said at least two actuators are hydraulic cylinders.

15. The X-ray chair in claim 4 wherein said at least two actuators move said X-ray chair into a trendelenburg position.

16. The X-ray chair in claim 4 wherein at least one rail is attached to said X-ray chair and said at least one rail is transparent to X-ray radiation.

* * * * *